United States Patent
Krüger et al.

(10) Patent No.: US 12,285,569 B2
(45) Date of Patent: Apr. 29, 2025

(54) CARBON DIOXIDE ABSORBER FOR A REBREATHER

(71) Applicant: Dräger Safety AG & Co. KGaA, Lübeck (DE)

(72) Inventors: Lorenz Krüger, Lübeck (DE); Christopher Libicher, Lübeck (DE); Tim Weber, Lübeck (DE)

(73) Assignee: DRÄGER SAFETY AG & CO. KGAA, Lübeck (DE)

( * ) Notice: Subject to any disclaimer, the term of this patent is extended or adjusted under 35 U.S.C. 154(b) by 908 days.

(21) Appl. No.: 17/368,009

(22) Filed: Jul. 6, 2021

(65) Prior Publication Data
US 2022/0008686 A1 Jan. 13, 2022

(30) Foreign Application Priority Data
Jul. 7, 2020 (DE) .......................... 102020117894.8

(51) Int. Cl.
*A61M 16/22* (2006.01)
*A62B 19/00* (2006.01)

(52) U.S. Cl.
CPC ............. *A61M 16/22* (2013.01); *A62B 19/00* (2013.01); *A61M 2205/3606* (2013.01); *A61M 2205/583* (2013.01)

(58) Field of Classification Search
CPC ......... A62B 19/00; A61M 16/22; G01F 23/02
See application file for complete search history.

(56) References Cited

U.S. PATENT DOCUMENTS

| 1,781,664 A | * | 11/1930 | Rockwell | ............... A62B 21/00 |
| | | | | 252/190 |
| 3,088,810 A | * | 5/1963 | Hay | ....................... A62B 19/00 |
| | | | | 128/205.28 |
| 3,612,048 A | * | 10/1971 | Takaoka | ............. A61M 16/104 |
| | | | | 128/205.12 |

(Continued)

FOREIGN PATENT DOCUMENTS

| DE | 60221087 T2 | 3/2008 |
| DE | 102011014267 B4 | 7/2014 |

(Continued)

OTHER PUBLICATIONS

Sodasorb Brochure, Molecular Filtration Group, accessed May 8, 2024 (Year: 2024).*

*Primary Examiner* — Kathryn E Ditmer
(74) *Attorney, Agent, or Firm* — McGlew and Tuttle, P.C.

(57) ABSTRACT

A carbon dioxide absorber (1) and a closed-circuit breathing apparatus (2) with the carbon dioxide absorber are based on the carbon dioxide absorber having an inlet (3) and an outlet (4) gas-tight connectable by a flow duct (5), in which a material (6) is arranged, which absorbs some carbon dioxide contained in the breathing gas stream sent through the material. The flow duct (5) is enclosed in some areas by a housing (7), in which a window element (8) is arranged. A display element (9) arranged movably in the flow duct (5) is visible through the window element from outside of the housing and/or through which window element the radiation reflected by the display element (9) exits to the outside. A distance between the window element (8) and the display element (9) varies as a function of the quantity of carbon dioxide-absorbing material arranged in the flow duct (5).

18 Claims, 2 Drawing Sheets

(56) References Cited

U.S. PATENT DOCUMENTS

| | | | | |
|---|---|---|---|---|
| 4,108,172 A * | 8/1978 | Moore, Jr. | A61M 16/22 | 128/205.12 |
| 4,350,662 A * | 9/1982 | Dowgul | B63C 11/24 | 128/205.12 |
| 4,781,184 A * | 11/1988 | Fife | A62B 7/10 | 128/205.12 |
| 5,038,768 A * | 8/1991 | McGoff | A62B 27/00 | 128/205.12 |
| 5,194,747 A * | 3/1993 | Culpepper | G01F 23/292 | 250/577 |
| 5,291,031 A * | 3/1994 | MacDonald | G01F 23/68 | 250/577 |
| 5,614,831 A * | 3/1997 | Edvardsson | G01F 23/284 | 73/290 V |
| 6,002,133 A | 12/1999 | Nelson et al. | | |
| 6,339,468 B1 * | 1/2002 | Clifford | G11B 5/5504 | 73/290 R |
| 7,635,854 B1 * | 12/2009 | Babin | G01F 23/2928 | 250/573 |
| 2010/0031753 A1 * | 2/2010 | Mayer | G01F 1/663 | 73/290 R |
| 2011/0026015 A1 * | 2/2011 | Mimeault | G01S 7/4866 | 356/139.1 |
| 2014/0345610 A1 | 11/2014 | Unger et al. | | |
| 2017/0219406 A1 * | 8/2017 | Akimov | G01F 23/804 | |

FOREIGN PATENT DOCUMENTS

| | | | | |
|---|---|---|---|---|
| DE | 102013018588 B3 | 2/2015 | | |
| DE | 102013016601 B4 | 9/2015 | | |
| DE | 102014103378 A1 * | 9/2015 | | G01F 23/02 |
| DE | 102014017634 A1 * | 6/2016 | | A62B 7/02 |
| DE | 102021113925 A1 * | 12/2022 | | |
| GB | 901334 A * | 7/1962 | | |
| GB | 976768 A * | 12/1964 | | |
| WO | 9220404 A1 | 11/1992 | | |

* cited by examiner

CARBON DIOXIDE ABSORBER FOR A REBREATHER

CROSS REFERENCE TO RELATED APPLICATIONS

This application claims the benefit of priority under 35 U.S.C. § 119 of German Application 10 2020 117 894.8, filed Jul. 7, 2020, the entire contents of which are incorporated herein by reference.

TECHNICAL FIELD

The present invention pertains to a carbon dioxide absorber with an inlet and with an outlet, which can be connected to a closed-circuit breathing apparatus (rebreather) and which are connected to one another in a gas-tight manner by a flow duct, in which a material is arranged, which absorbs at least some of the carbon dioxide contained in a breathing gas stream sent through the material. Such carbon dioxide absorbers can be used both in closed-circuit respirators, as they are used, for example, in mine rescue operations, or in closed-circuit diving apparatuses.

TECHNICAL BACKGROUND

It is essential for the closed-circuit breathing apparatuses (rebreathers) known from the state of the art that the user of the apparatus is supplied with oxygen independently from the ambient atmosphere, and the needed breathing gas is generated within the apparatus, unlike in respirators operating with compressed air. After the exhalation of the breathing gas sent to the user of the apparatus, this breathing gas is processed in a circuit located within the apparatus before it is fed again to the user of the apparatus, and carbon dioxide is removed in the process from the exhaled breathing gas during the processing and oxygen is fed. Closed-circuit breathing apparatuses are usually carried on the back or on the abdomen and are connected to the breathing mask via breathing tubes, via which the user of the apparatus inhales and exhales. Either compressed oxygen or oxygen generated from chemicals is carried as the oxygen source. The removal of the carbon dioxide ($CO_2$) exhaled by the user of the apparatus takes place in the prior-art closed-circuit breathing apparatuses by means of the so-called breathing lime, which is carried out in cartridges, which may be configured as disposable articles or as refillable cartridges. A granular mixture of calcium hydroxide ($Ca(OH)_2$) and sodium hydroxide (NaOH) or of potassium hydroxide (KOH) and barium hydroxide ($Ba(OH)_2$) is used, as a rule, as breathing lime.

While the breathing gas exhaled by the user of the apparatus flows through the bulk breathing lime within the breathing lime cartridge, the carbon dioxide present in the breathing gas is absorbed and heat and water are generated. Breathing lime commonly used absorbs 10 L to 15 L of carbon dioxide per 100 g of bulk material. In order to guarantee a satisfactory, reliable operation of a carbon dioxide absorber, a sufficient quantity of breathing lime, which is capable of absorbing carbon dioxide, must always be contained in the breathing lime cartridge carried along.

A closed-circuit breathing apparatus of this class is known from DE 10 2011 014 267 B4. The closed-circuit breathing apparatus described has a housing as well as breathing tubes for feeding and removing breathing air into and out of a breathing mask. The breathing gas exhaled by the user of the apparatus is sent through a breathing lime cartridge, in which carbon dioxide is removed from the exhaled breathing gas stream. A small quantity of oxygen is fed into the breathing gas downstream of the breathing lime cartridge from a compressed gas cylinder and the breathing gas thus processed is finally sent again to the user of the apparatus via the breathing gas.

Furthermore, a device as well as a process for determining the degree of saturation of breathing lime are known from DE 10 2013 018 588 B3. The device described has a radiation source, which emits radiation with at least two different wavelengths, a sensor, a data processing unit and a light conductor, which is arranged at least partially in a breathing lime cartridge filled with breathing lime. The radiation emitted by the radiation source is coupled into the light conductor and from here into the breathing lime arranged within the breathing lime cartridge. The radiation reflected by the light conductor is coupled again into the light conductor and is sent through the light conductor to the sensor, and a degree of saturation of the breathing lime is finally determined from the intensity of the reflected radiation. It is thus possible with the device described to determine the degree of saturation or the still available binding capacity of the breathing lime.

There always is a risk during the use of closed-circuit breathing apparatuses that the breathing lime is saturated, i.e., that its capacity to absorb carbon dioxide is exhausted, or that the necessary breathing lime cartridge is not inserted or is not inserted correctly into the closed-circuit breathing apparatus. There is for this reason a general need for informing the user of the apparatus in the simplest and most reliable solution manner on whether and possibly for how long a closed-circuit breathing apparatus is usable.

The closed-circuit diving apparatus Explorer from the Hollis company, which has a display informing the user of the apparatus of whether a carbon dioxide absorber is present in the apparatus is known in this connection. As soon as a breathing lime cartridge is inserted into the apparatus, this presses against the force of a spring a display pin, which will then move outwards and is visible through a window. It is displayed in this manner to the user that a breathing lime cartridge, inserted properly, is present in the apparatus. However, the user of the apparatus does not receive any information on the filling level or the still remaining carbon dioxide absorption capacity of the inserted breathing lime cartridge based on this display.

SUMMARY

Based on the solutions known from the state of the art as well as on the above-described problems, a basic object of the present invention is to provide a carbon dioxide absorber, in which the filling level of the breathing lime, which is present in the interior, can be detected in a simple and reliable manner. In particular, a visual checking shall be possible, without the carbon dioxide absorber having to be taken apart and/or opened for this purpose. The technical solution to be proposed should thus make it possible for a user in a simple and reliable manner to visually perceive the filling level of a breathing lime cartridge from the outside. Furthermore, the technical solution should create a possibility of visually detecting the filling level of a carbon dioxide absorber mounted in the apparatus without opening a closed-circuit breathing apparatus (rebreather). It is always especially significant in this connection that a user is able to clearly detect, especially before putting a closed-circuit breathing apparatus into operation, whether a breathing lime cartridge is present in the apparatus and whether an inserted breathing lime cartridge is filled properly in order to be able to absorb carbon dioxide to the necessary extent and in order to guarantee a reliable operation for a user of the apparatus.

Furthermore, a corresponding display unit should require little maintenance, should make possible an undisturbed operation over the longest time period possible, and have a comparatively simple structural configuration, so that the manufacturing costs can also be kept within economically acceptable limits. A corresponding display should be able to be made possible in an advantageous manner without additional energy, especially in the form of electrical energy, being needed for this.

The above-mentioned object is accomplished with a carbon dioxide absorber according to the invention as well as with a closed-circuit breathing apparatus with such a carbon dioxide absorber. Advantageous embodiments of the present invention will be explained in more detail in the following description partially with reference to the figures.

The present invention pertains to a carbon dioxide absorber with an inlet and with an outlet, which can be connected to a closed-circuit breathing apparatus, especially to the breathing gas circuit thereof, and which are connected to one another in a gas-tight manner by a flow duct, in which a material that absorbs at least some of the carbon dioxide contained in the breathing gas stream sent through the material is arranged. The carbon dioxide absorber is characterized according to the present invention in that the flow duct is enclosed in at least some areas by a housing, in which a window element is arranged, through which a display element arranged movably in the flow duct is visible from the outside of the housing and/or through which radiation reflected by the display element exits, wherein a distance between the window element and the display element varies as a function of the quantity of carbon dioxide-absorbing material arranged in the flow duct. Essential is thus the combination of a window element, which allows the view into the interior of the housing of a carbon dioxide absorber with the carbon dioxide-absorbing material arranged therein, and a display element arranged in the interior of the housing, with the display element position changing as a function of the quantity of carbon dioxide-absorbing material filled in, especially breathing lime, such that a distance between the window element and the display element likewise changes thereby as well. The movement of the display element in the interior of the housing of the carbon dioxide absorber takes place in this case as a function of the filling level or the quantity of carbon dioxide-absorbing material filled in, in such a controlled manner, that on looking into the window element, the display element and/or a radiation reflected by same become visible to the user of the apparatus such that the user receives information on the current filling level or the quantity of carbon dioxide-absorbing material filled in from the arrangement of the display element relative to the window element and/or on the basis of a display object, for example, a special light object, which is caused by radiation emitted by the display element. If a carbon dioxide absorber configured according to the present invention is installed in a closed-circuit breathing apparatus, which offers, on the one hand, the possibility of detecting the window element from the outside, without a housing of the closed-circuit breathing apparatus having to be opened for this purpose, a user and/or a user of the apparatus can, further, both detect whether a carbon dioxide absorber is present in the interior of the closed-circuit breathing apparatus and also obtain information on the filling level in the carbon dioxide absorber. It is thus likewise unnecessary to open or to remove the closed-circuit breathing apparatus and/or the carbon dioxide absorber.

It is especially advantageous if the display element is configured such that it can be detected from the outside through the window element, without the display element itself having a light source. The surface is preferably configured therefore such that entering radiation is reflected in the direction of the window element.

Further, a carbon dioxide absorber configured according to the present invention is preferably configured in the form of a cartridge, which has an inlet and an outlet, at which the breathing gas circuit of a closed-circuit breathing apparatus, either of a closed-circuit respirator, as it is used in mine rescue operations, or of a closed-circuit diving apparatus, can be connected in a gas-tight manner (gas-tight connected). The inlet and/or the outlet advantageously have for this purpose suitable connection elements, which make it possible to connect a breathing lime cartridge to the breathing gas circuit rapidly and in a reliable manner. Establishment of a connection by means of a quarter-turn fastener or threaded closure is conceivable as well.

Provisions are made according to a special embodiment of the present invention for the display element to be arranged on a pressing unit, which is movable within the flow duct and which is indirectly or directly in contact with the absorber material. In this connection the display element may be fastened on or at the pressing unit or is made in one piece with the pressing unit. The pressing unit is arranged movably within the flow duct with the carbon dioxide-absorbing material located therein such that a specific movement takes place when the filling level or the quantity of carbon dioxide-absorbing material filled into the flow duct changes. The pressing unit is preferably acted on by a spring force, said spring force acting on the pressing unit such that the pressing unit is pushed or even moved in the direction of the carbon dioxide-absorbing material. The spring element is configured in this case preferably such that only a weak spring force is exerted in the direction of the material arranged in the interior of the carbon dioxide absorber and a comparatively weak force will thus act on the material. Based on the spring force acting on the pressing unit, the latter is moved when the filling level or the quantity of material filled into the carbon dioxide absorber changes, especially in case of a reduction of the filling level or of the quantity filled in, and the distance between the window element and the display element connected indirectly or directly to the pressing unit will thus change as well.

According to another special embodiment, the pressing unit has, in at least some areas, a screen element, which is in contact with the carbon dioxide-absorbing material. Furthermore, the pressing unit may be in contact with the wall of the flow duct at least in some areas at its outer circumference, especially indirectly via a sealing element, which is in contact with the wall of the flow duct. The material arranged in the flow duct is thus pushed together by means of the pressing unit during a change in the quantity filled in or in the filling level, so that the breathing gas from which carbon dioxide is to be removed will continue to flow through the material in a suitable manner.

In a special variant of the present invention, at least one mark is arranged on the window element. In this connection such a mark may have a measuring scale, a linear scale, concentric circles and/or crosshairs. The mark makes it possible for the user of the apparatus to read the particular filling level or the quantity of the absorber material filled into the interior of the carbon dioxide absorber in a comparatively simple manner. For example, the mark has crosshairs or a plurality of concentric circles, which are more or less covered by an image of the display element depending on the distance of the display element from the window element. It is essential for this technical solution that an outer contour of the display element or the image thereof on the window element is put into relation to the mark, so that unambiguous and easy-to-detect information is outputted to the user of the apparatus in relation to the filling level or the quantity of carbon dioxide-absorbing material filled in.

In another special embodiment of the present invention, the display element has at least one opaque material, so that the display element is not transparent or is only partially transparent to impacting radiation. Such a material is preferably a plastic, a mixture of different plastics and/or a crystalline material. It is significant for the opaque material used that this is not fully transparent to impacting radiation, but it reflects radiation at least in a part of the range of the rays of the radiation. Opaque material is characterized here generally by the fact that such opaque material possesses scattering properties for at least some of the impacting radiation.

In a very special embodiment of the present invention, an optical element is provided, by which the light beam entering the window element from the outside is deflected divergently away from a central axis extending from the window element to the display element, so that the radiation propagating from the window element to the display element diverges. The optical element is preferably a lens and/or a prism, by which impacting radiation is deflected and/or formed in a suitable manner. The optical element used may be arranged between the window element and the display element or is integrated into the window element. Provisions are made in this connection by a very special variant of the present invention for the window element to be configured in at least some areas in the form of an optical element, which deflects the radiation entering into the window element from the outside from a surrounding area divergently from a central axis extending from the window element to the display element. The window element is thus preferably configured such that impacting light beams are refracted at the respective edges, which represent transitions between different media, i.e., especially at the transition between the window element and the interior space of the carbon dioxide absorber, such that the radiation propagating in the interior space will diverge. It is essential that the radiation is refracted both at the time of entry into the window element and at the time of exit from this. The greater the distance of the display element from the body edge of the window element, which body edge faces the display element. i.e., the greater the distance between the window element and the display element, the smaller is the number of light beams impacting on the display element and that are reflected by this. It follows from this that the image of the display element, which image is perceptible through the window element, decreases steadily during the operation of a closed-circuit breathing apparatus and during the accompanying decrease of the filling level of the absorber material being used, until it ceases to be perceptible any longer, because the distance between the display element and the window element has become too great. According to this special embodiment of the present invention, the distance between the display element and the window element is used to generate an image of the display element in the area of the window element, the size of the image being put into relation to the filling level of the carbon dioxide absorber. In a special embodiment, different filling levels correspond to respective different image diameters, and the radius of an image of the display element in the area of the window element can preferably be calculated as a function of the distance between the window element and the display element.

In a special embodiment of the present invention, a carbon dioxide-absorbing material, which is configured as a bulk material, is located in the flow duct of the carbon dioxide absorber, through which flow duct the breathing gas to be processed flows. The material used to absorb carbon dioxide, i.e., the so-called breathing lime, is preferably a mixture of calcium hydroxide ($Ca(OH)_2$) and sodium hydroxide (NaOH) or of calcium hydroxide (KOH) and barium hydroxide ($Ba(OH)_2$). The absorber material may be discarded after the absorption capacity of the absorber material has been depleted, or absorber material may be provided in a refillable reusable container in the carbon dioxide absorber. In this connection the flow duct enclosed by the housing may have at least one closable filling opening, through which the absorber material can be filled in and/or removed at least from time to time.

The present invention is otherwise accomplished with a closed-circuit breathing apparatus, which has a carbon dioxide absorber, which is configured in accordance with at least one of the above-described embodiments. The closed-circuit breathing apparatus may be configured either as a closed-circuit respirator, e.g., as used in rescue operations, especially in mine rescue operations, or as a closed-circuit diving apparatus. It is essential in each case that the carbon dioxide absorber is connected via its inlet and the outlet to the breathing gas circuit of the closed-circuit breathing apparatus such that at least some of the carbon dioxide contained in the breathing gas can be removed from the breathing gas exhaled by a user of the apparatus. The closed-circuit breathing apparatus advantageously likewise has, especially in the area of a closed-circuit breathing apparatus housing, at least one window element, which in turn allows the view to the window element of the carbon dioxide absorber and hence at least indirectly to the display element. The user of the apparatus thus can read the filling level of the carbon dioxide absorber, especially before putting the apparatus into operation, without having to open the closed-circuit breathing apparatus for this. It is further conceivable that a closed-circuit breathing apparatus configured according to the present invention can be equipped with a disposable or reusable cartridge as a carbon dioxide absorber.

The present invention will be explained in more detail below without limitation of the general inventive idea on the basis of exemplary embodiments with reference to the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
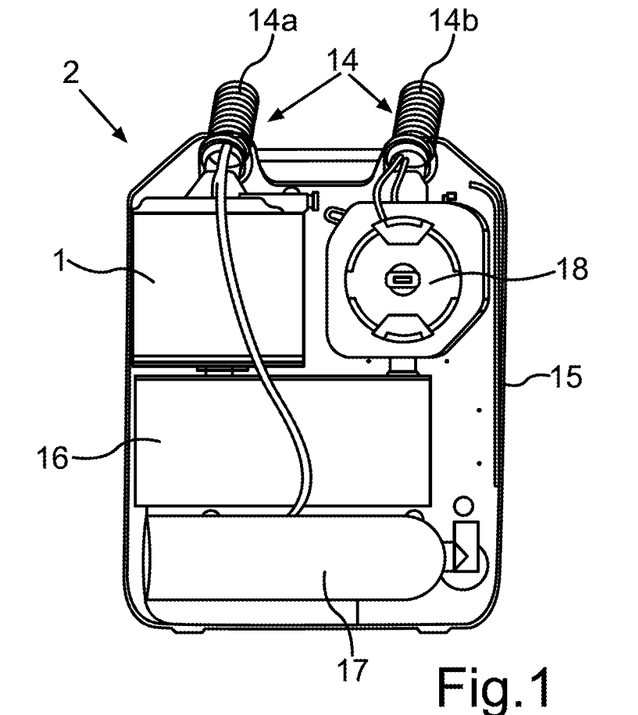
FIG. 1 is a schematic view of a closed-circuit breathing apparatus (rebreather) with a carbon dioxide absorber configured according to the present invention.

Referring to the drawings, FIG. 1 shows a closed-circuit breathing apparatus (rebreather) 2, in which a carbon dioxide absorber 1 configured according to the present invention is installed. The closed-circuit breathing apparatus 2 has two breathing tubes 14 for feeding and removing breathing gas into and out of a breathing mask, not shown, which is used by a user of the apparatus. Of the two breathing tubes 14, the breathing tube arranged on the right side is the inhalation tube 14b, and the breathing tube arranged on the left side is the exhalation tube 14a.

Both breathing tubes 14 are connected to a housing 15 of the closed-circuit breathing apparatus 2. A carbon dioxide absorber 1 is arranged in the housing 15 for at least partially removing the carbon dioxide ($CO_2$) exhaled by the user of the apparatus during the use of the closed-circuit breathing apparatus 2. A breathing bag 16 is attached to the housing 15 under the carbon dioxide absorber 1. Furthermore, an oxygen source 17, which is formed by a pressurized oxygen gas cylinder, is arranged in the embodiment shown within the housing 15. Since heat is generated during the absorption of carbon dioxide ($CO_2$), the closed-circuit breathing apparatus 2 shown in FIG. 1 has a breathing gas cooler 18, which removes the heat generated during the absorption of the carbon dioxide from the closed breathing circuit at least partially. The breathing gas circuit is comprised of both breathing tubes 14, the carbon dioxide absorber 1, the breathing bag 16, the oxygen source 17 and the breathing gas cooler 18. During the operation of the closed-circuit breathing apparatus 2 shown in FIG. 1, the breathing gas exhaled by the user of the apparatus enters via the exhalation tube 14a at first the carbon dioxide absorber 1, where it is freed at least partially of the carbon dioxide ($CO_2$) contained in the breathing gas by the carbon dioxide-absorbing material 6 arranged at the carbon dioxide absorber 1, absorbing a part of the carbon dioxide while heat and water are generated. The breathing gas is then sent into the breathing bag 16, in which the oxygen used up by the user of the apparatus is replaced with oxygen from the pressurized oxygen gas cylinder carried along as a source of oxygen 17. The breathing gas, which is freed from excess carbon dioxide and is enriched with oxygen, then flows through the breathing gas cooler 18, in which a part of the heat of reaction released during the absorption of carbon dioxide is removed from the breathing gas circuit. The breathing gas regenerated as described above is sent via the inhalation tube 14b into a breathing mask, not shown, via which it is inhaled by the user of the apparatus.

Figure 2:
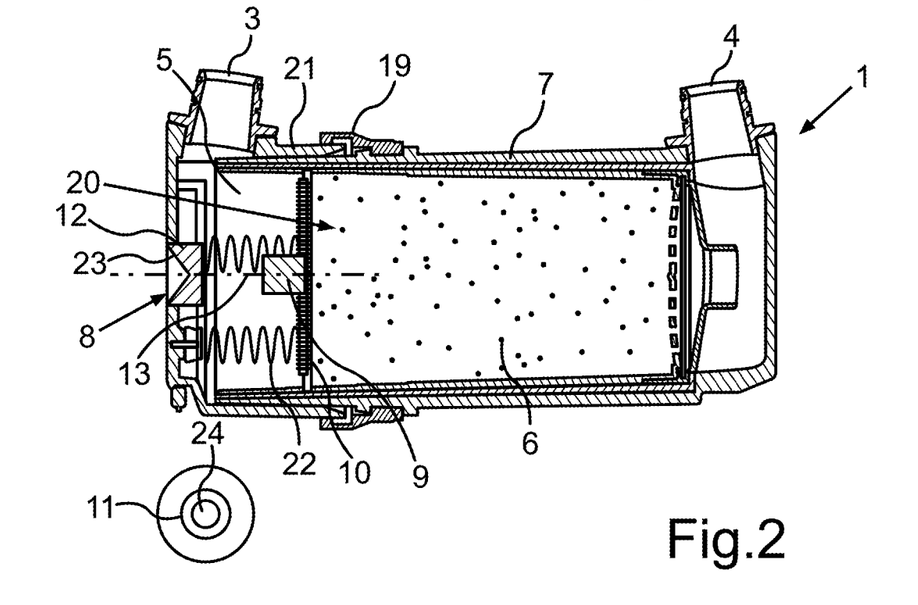
FIG. 2 is a sectional view of a carbon dioxide absorber configured according to the present invention.

FIG. 2 shows a carbon dioxide absorber 1 configured according to the present invention. Such carbon dioxide absorbers 1 may be configured as a disposable or reusable cartridge. The carbon dioxide absorber 1 is configured as a reusable cartridge in the embodiment shown in FIG. 2. The carbon dioxide absorber 1 can be opened by actuating a closing element, and the housing 7 is taken apart into two parts in the case being shown. The cover element 21 together with the window element 8 and with some components, here a spring element 22 and a pressing unit 10 with a display element 9, which are fastened to the cover element 21 and are arranged in the flow duct 5 in the closed state, are removed now. A filling opening 20, having a size corresponding to the external diameter of the flow duct 5 in the area of the separation point of the housing 7 and through which the carbon dioxide-absorbing material 6 can be removed, especially in the saturated state, and new, unsaturated material 6 can be introduced into the flow duct, is released in this manner.

The carbon dioxide absorber 1 shown has an inlet 3 and an outlet 4, which can be connected to the breathing gas circuit of a closed-circuit breathing apparatus 2, as it is shown, for example, in FIG. 1, at least in a largely gas-tight manner. The inlet 3 and the outlet 4 are connected via the flow duct 5, in which carbon dioxide-absorbing material 6, the so-called breathing lime, is arranged in the form of a granular bulk material as an absorber material. For example, a mixture of calcium hydroxide ($Ca(OH)_2$) and sodium hydroxide (NaOH) or of potassium hydroxide (KOH) and barium hydroxide ($Ba(OH)_2$) is used as the carbon dioxide-absorbing material.

A disk-shaped pressing unit 10 is arranged movably in the interior of the flow duct 5, and this is pushed against the absorber material 6 by means of a spring element 22, which has two coil springs. A display element 9 is fastened on the pressing unit 10 arranged movably in the flow duct 5 in the form of a cuboid, which has a red-colored, opaque plastic material. Depending on the quantity of the absorber material 6 filled in within the flow duct 5, the distance between the display element 9 and the window element 8, which is arranged in the housing 7 enclosing the flow duct 5, varies, and the distance becomes greater in case of a smaller quantity of filling.

The window element 8 shown in FIG. 2 is arranged in the wall of the housing 7 such that the window element 8 allows the view to the display element 9 from an area surrounding the carbon dioxide absorber 1. It is thus possible by a visual checking, i.e., by the view through the window element 8, to check the filling level of the carbon dioxide absorber 1 without this having to be opened for this purpose. A user is thus able to check the filling level in a simple manner, especially prior to the putting into operation of the closed-circuit breathing apparatus 2. It is essential for the present invention in this connection that the distance between the window element 8 and the display element 9 varies as a function of the filling level, so that the size of the image of the display element 9, which image is visible in the window element 8, changes likewise. The smaller the visible image, the lower is the filling level of the carbon dioxide-absorbing material 6 in the carbon dioxide absorber 1 and the lower is consequently the capacity of the material 6 to absorb carbon dioxide. In the extreme case, in which no image of the display element 9 can be detected in the window element, the user can assume that the carbon dioxide absorber 1 no longer contains a sufficient quantity of carbon dioxide-absorbing material 6 for a reliable operation.

Exhaled breathing air flows through the inlet 3 into the carbon dioxide absorber 1 during the operation of the carbon dioxide absorber 1 shown in FIG. 2, for example, in a breathing circuit of a closed-circuit breathing apparatus. The breathing air enriched with carbon dioxide, which is exhaled by the user of the apparatus, then flows through the absorber material 6, which is arranged in the flow duct 5 of the carbon dioxide absorber 1, and which is formed in this case from a mixture of calcium hydroxide ($Ca(OH)_2$) and sodium hydroxide (NaOH), and the following reactions take place:

$$CO_2 + H_2O \leftrightarrow H_2CO_3$$

$$H_2CO_3 + 2NaOH \leftrightarrow Na_2CO_3 + H_2O$$

$$Na_2CO_3 + Ca(OH)_2 \leftrightarrow CaCO_3 + 2NaOH$$

Carbon dioxide is removed now from the breathing gas stream while water is formed and heat is generated. The filling level of the absorber material 6 decreases during continuing operation of a closed-circuit breathing apparatus 2 with the carbon dioxide absorber 1 arranged therein. Based on this change in the filling level, the pressing unit 10, which is pushed, acted on by spring force, against the absorber material, moves to the right, as a result of which the distance between the window element 8 and the display element 9 increases. The detail view "A" shows for this a top view of the window element 8, on which a mark 11 with a plurality of concentric circles is located and in which a centrally oriented image of the display element 9 can be seen. The greater the distance between the window element 8 and the display element becomes, the smaller will be the image of the display element 9 within the window element 8. Based on the mark 11 provided on the window element 8 with concentric circles, having a radius always selected as a function of a defined distance between the window element 8 and the display element, a change in the distance and hence in the filling level of carbon dioxide-absorbing material 6 can be detected by a user rapidly and accurately.

It is especially advantageous if a closed-circuit breathing apparatus, in which the carbon dioxide absorber shown in FIG. 2 is arranged, also has a window, through which a user, especially the user of the apparatus, can look at the window element 8 of the carbon dioxide absorber 1 from the outside from an area surrounding the apparatus and can thus detect the image of the display element 9, without having to open the closed-circuit breathing apparatus 2. It is consequently unnecessary in this case to open the closed-circuit breathing apparatus 2 in order to check the filling level of the particular installed carbon dioxide absorber.

The window element 8 is configured such that an optical element 12, which possesses light-refracting properties, is integrated into this, wherein the light beams are always refracted at the edges of the window element 8, at which different media adjoin one another. The optical element 12 is configured such that light beams impacting on the window element 8 from the outside from a surrounding area are deflected divergently from a central axis 13, which extends from the window element 8 to the display element 9, after the passage through the optical element 12 integrated into the window element 8. The principle of operation employed here is shown in FIGS. 3a, 3b and 3c.

If light beams 25 from the outside from the surrounding area reach the window element 8 with the optical element 12, the light beams 25 are refracted at the edge 23 facing the display element 9 during the transition from the optical more dense medium to the optically thinner medium such that the light beams 25 are deflected divergently away from a central axis 13 extending between the window element 8 and the display element 9. FIG. 3a shows in this connection in a schematic sectional view the window element 8, the display element 9 arranged at a spaced location therefrom in the interior space of the carbon dioxide absorber 1 as well as an image 24 of the display element 9, which image 24 can be detected when viewing the window element 8. The image 24 of the display element 9, which is shown in FIG. 3a, is perceptible in case of an at least nearly maximum filling level and hence minimal distance between the window element 8 and the display element 9.

As was explained already, the distance of the display element 9 from the window element 8 changes as a function of the carbon dioxide-absorbing material 6 filled in, which is arranged within the carbon dioxide absorber 1.

Figure 3A:
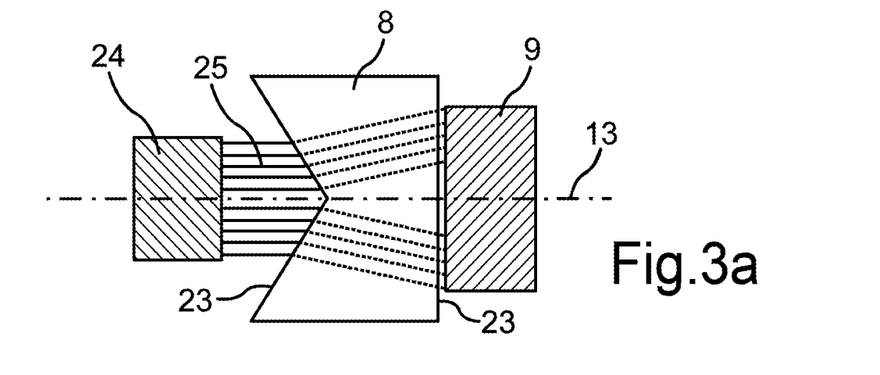
FIG. 3a is a schematic view showing an aspect of the principle of operation for the detection of the filling level of a carbon dioxide absorber configured according to the present invention with the use of a change in the distance between a window element and a display element.
Figure 3B:
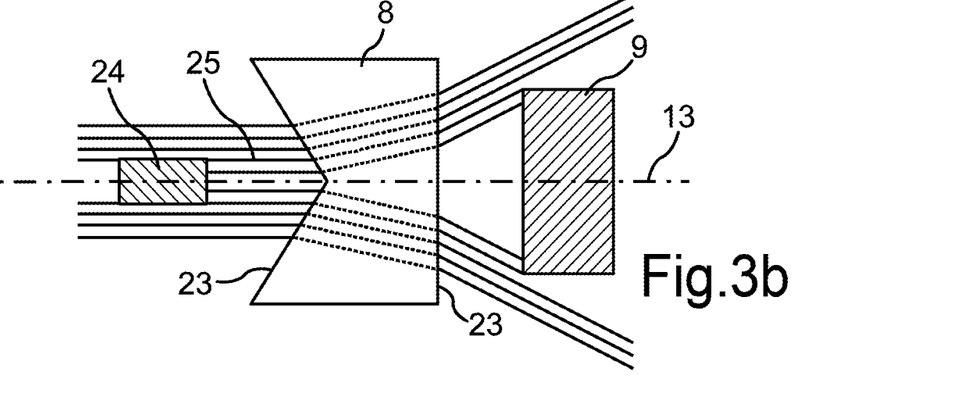
FIG. 3b is a schematic view showing another aspect of the principle of operation for the detection of the filling level of a carbon dioxide absorber configured according to the present invention with the use of a change in the distance between a window element and a display element.
Figure 3C:
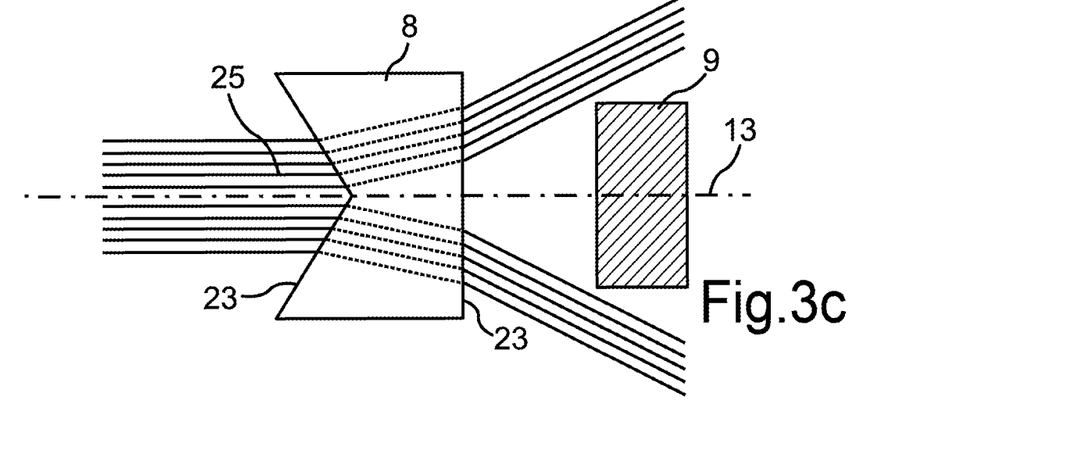
FIG. 3c is a schematic view showing another aspect of the principle of operation for the detection of the filling level of a carbon dioxide absorber configured according to the present invention with the use of a change in the distance between a window element and a display element.

FIG. 3b shows for this an operating state in which the filling level of the absorber material 6 has decreased compared to the operating state shown in FIG. 3a. It can be seen that the image 24 of the display element 9, which image is visible in the window element, is markedly smaller than the image shown in FIG. 3a. This can be attributed to the fact that some of the light beams 25 irradiated into the interior of the carbon dioxide absorber, which are deflected divergently from a central axis 13 extending between the window element 8 and the display element 9, do not fall on the display element 9 and are thus also reflected. A viewer, who is looking into the window element 8, will see that the size of the image 24 of the display element 9 has decreased markedly compared to the image according to FIG. 3a and this viewer will infer from this a reduction of the filling level of the carbon dioxide-absorbing material 6 in the carbon dioxide absorber 1, which has taken place in the meantime between the operating states according to FIG. 3a and FIG. 3b.

FIG. 3c shows another operating state, in which the filling level of the absorber material 6 arranged in the carbon dioxide absorber 1 is lower compared to the operating state according to FIG. 3b or no breathing lime may possibly even be contained in the carbon dioxide absorber 1. The distance between the window element 8 and the display element 9 has likewise continued therefore to increase. The distance between the window element 8 and the display element 9 is so great now that light beams 25 falling into the window element 8, which are deflected divergently away from the central axis extending between the window element 8 and the display element, travel completely past the display element, so that no radiation is reflected by the display element 9 in the direction of the window element 8. Thus, no image of the display element 9 appears in the window element, so that a user looking at the window element 8 receives the information that the filling level of the absorber material 6 within the carbon dioxide absorber 1 is so low that new absorber material 6 must be added or another carbon dioxide absorber 1 must be used.

It is essential that it is not necessary based on the display provided according to the present invention to open a carbon dioxide absorber 1 or possibly a closed-circuit breathing apparatus in order to obtain information on the filling level of the absorber material 6.

While specific embodiments of the invention have been shown and described in detail to illustrate the application of the principles of the invention, it will be understood that the invention may be embodied otherwise without departing from such principles.

LIST OF REFERENCE NUMBERS

1 Carbon dioxide absorber
2 Closed-circuit breathing apparatus
3 Inlet
4 Outlet
5 Flow duct
6 Carbon dioxide-absorbing material
7 Housing
8 Window element
9 Display element
10 Pressing unit
11 Mark
12 Optical element
13 Central axis
14 Breathing tube
   14a Exhalation tube
   14b Inhalation tube
15 Housing of the closed-circuit breathing apparatus
16 Breathing bag
17 Oxygen source
18 Breathing gas cooler
19 Closing element
20 Filling opening
21 Cover element
22 Spring element
23 Edge of the window element
24 Image of the display element
25 Light beams

What is claimed is:

1. A carbon dioxide absorber comprising:
an inlet;
an outlet, the inlet and the outlet being connectable to a closed-circuit breathing apparatus;
a flow duct gas-tight connecting the inlet and the outlet;
carbon dioxide absorbing material arranged in the flow duct to absorb at least some carbon dioxide contained in a breathing gas stream sent through the carbon dioxide absorbing material;
a housing enclosing the flow duct in at least some areas;
a window element arranged at the housing;
a display element arranged movably in the flow duct, the display element being visible from outside of the housing through the window element and/or configured such that radiation reflected by the display element exits to the outside of the housing through the window element, wherein a distance between the window element and the display element is configured to vary as a function of a quantity of carbon dioxide-absorbing material arranged in the flow duct; and
an optical element through which a light beam entering the window element from the outside from a surrounding area is configured to be deflected divergently from a central axis extending from the window element to the display element.

2. The carbon dioxide absorber in accordance with claim 1, wherein the display element is associated with a pressing unit arranged movably within the flow duct, the pressing unit being indirectly or directly in contact with the carbon dioxide absorbing material.

3. The carbon dioxide absorber in accordance with claim 2, wherein the display element is arranged on the pressing unit and is acted on by a spring force to push and/or pull the display element toward the carbon dioxide absorbing material.

4. The carbon dioxide absorber in accordance with claim 2, wherein the pressing unit has a screen configuration in at least some areas.

5. The carbon dioxide absorber in accordance with claim 2, wherein a mark is arranged on the window element.

6. The carbon dioxide absorber in accordance with claim 2, wherein the display element comprises at least one opaque material.

7. The carbon dioxide absorber in accordance with claim 1, wherein the optical element comprises at least one of a lens and a prism.

8. The carbon dioxide absorber in accordance with claim 1, wherein the optical element is integrated into the window element.

9. The carbon dioxide absorber in accordance with claim 2, wherein the carbon dioxide absorbing material is configured as a bulk material.

10. The carbon dioxide absorber in accordance with claim 2, wherein the carbon dioxide absorbing material comprises at least one of calcium hydroxide ($Ca(OH)_2$) and sodium hydroxide (NaOH).

11. The carbon dioxide absorber in accordance with claim 2, wherein the housing is a part of a disposable cartridge.

12. The carbon dioxide absorber in accordance with claim 2, wherein the flow duct comprises a closable filling opening through which the carbon dioxide absorbing material is configured to be at least one of filled in and removed.

13. A closed-circuit breathing apparatus comprising:
a breathing tube; and
a carbon dioxide absorber, the carbon dioxide absorber comprising:
an inlet;
an outlet, the inlet and the outlet being connectable to the breathing tube;
a flow duct gas-tight connecting the inlet and the outlet;
carbon dioxide absorbing material arranged in the flow duct to absorb at least some carbon dioxide contained in a breathing gas stream sent through the carbon dioxide absorbing material;
a housing enclosing the flow duct in at least some areas;
a window element arranged at the housing;
a display element arranged movably in the flow duct, the display element being visible from outside of the housing through the window element and/or configured such that radiation reflected by the display element exits to the outside of the housing through the window element, wherein a distance between the window element and the display element is configured to vary as a function of a quantity of carbon dioxide-absorbing material arranged in the flow duct; and
an optical element through which a light beam entering the window element from the outside from a surrounding area is configured to be deflected divergently from a central axis extending from the window element to the display element.

14. The closed-circuit breathing apparatus in accordance with claim 13, wherein the display element is associated with a pressing unit arranged movably within the flow duct, the pressing unit being indirectly or directly in contact with the carbon dioxide absorbing material.

15. The closed-circuit breathing apparatus in accordance with claim 14, wherein the display element is arranged on the pressing unit and is acted on by a spring force to push and/or pull the display element toward the carbon dioxide absorbing material.

16. The closed-circuit breathing apparatus in accordance with claim 14, wherein a mark is arranged on the window element.

17. The closed-circuit breathing apparatus in accordance with claim 14, further comprising a closed-circuit breathing apparatus housing, the breathing tube and the carbon dioxide absorber being connected to the closed-circuit breathing apparatus housing.

18. The closed-circuit breathing apparatus in accordance with claim 17, further comprising at least one additional component comprising at least one of a breathing bag, an oxygen source and a breathing gas cooler, wherein the at least one additional component is connected to the closed-circuit breathing apparatus housing.

* * * * *